United States Patent [19]
Rowean

[11] 4,022,217
[45] May 10, 1977

[54] CUFF CONFIGURATION FOR CUFF TRACHEAL TUBES

[75] Inventor: Donald R. Rowean, Poway, Calif.

[73] Assignee: Dupaco Incorporated, San Marcos, Calif.

[22] Filed: Sept. 15, 1975

[21] Appl. No.: 613,459

[52] U.S. Cl. .............................. 128/349 B; 128/351
[51] Int. Cl.² ...................................... A61M 25/00
[58] Field of Search ............... 128/349, 348, 349 B, 128/350, 129, 325, 246, 349 BV, 351, 324

[56] References Cited
UNITED STATES PATENTS

| | | | |
|---|---|---|---|
| 2,518,165 | 8/1950 | Millard | 128/DIG. 5 |
| 2,687,131 | 8/1954 | Raiche | 128/349 B |
| 3,509,884 | 5/1970 | Bell | 128/349 B |
| 3,799,173 | 3/1974 | Kamen | 128/351 |
| 3,854,484 | 12/1974 | Jackson | 128/351 |

*Primary Examiner*—Stephen C. Pellegrino
*Attorney, Agent, or Firm*—Christie, Parker & Hale

[57] ABSTRACT

A tracheal tube has a cuff surrounding its exterior for being filled with liquid or air to expand the cuff against a patient's trachea to provide a sealed air passage through the tube into the patient's lungs. The cuff, in its expanded configuration, has a bulbed anterior portion which seals against the trachea, and a narrow, elongated posterior portion extending distally away from the bulb. The cuff configuration allows the cuff to stay in a fixed position in the trachea during use, which reduces trauma and irritation to the patient.

20 Claims, 3 Drawing Figures

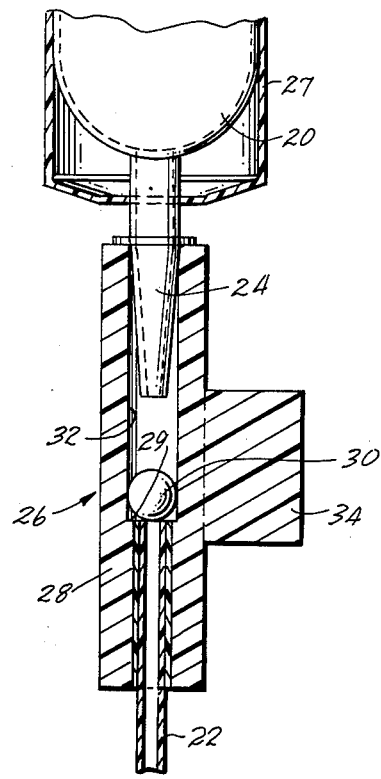
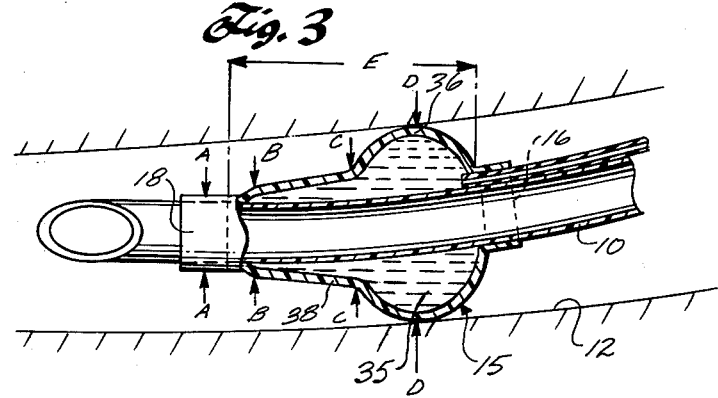

CUFF CONFIGURATION FOR CUFF TRACHEAL TUBES

BACKGROUND

This invention relates to endotracheal and tracheotomy tubes, hereafter referred to as tracheal tubes, and more particularly to an improved cuff configuration for tracheal tubes.

Tracheal tubes are used to provide an air-way through the trachea into the lungs of a patient during respirator therapy or general anesthesia. Hydraulic cuff tracheal tubes include a liquid-fillable, inflatable cuff surrounding the portion of the tube located in the trachea. During use, the cuff is filled with liquid to inflate the cuff so it seals against the patient's trachea. The hydraulic pressure applied to the cuff for inflation typically is provided by a collapsible liquid-filled reservoir or syringe being held at an elevation above the cuff which allows liquid to flow through a filling lumen and into the cuff. Hydraulic cuff tracheal tubes of this type produce a relatively small amount of pressure against the trachea, and are distinguished from pneumatic cuff tracheal tubes which generally do not have as precise control over the inflation pressure applied to the cuff. As a result, pneumatic cuff tracheal tubes, as well as hydraulic cuff tubes not having precise control over the filling pressure, produce considerable trauma to the patient.

Tracheal tubes are known generally, and are disclosed, for example, in U.S. Pat. Nos. 3,348,542; 3,766,927; and 3,854,484 to Jackson.

One difficulty with prior tracheal tubes is that the cuff in its collapsed condition is very floppy, which obscures visibility to the back of the mouth when the physician places the tube in the patient's trachea.

Another difficulty with prior tracheal tubes is that the cuff, when inflated, can move back and forth in the trachea in response to inhalation and exhalation of the patient, resulting in extreme trauma to the patient. For example, if the cuff, when inflated, is of generally uniform diameter and is relatively large in diameter relative to the tube, then a substantial effective area is provided between the ends of the inflated cuff. This area is sensitive to pressure differentials across the cuff as produced in the trachea during inhalation and exhalation phases of the patient's respiration cycle. These pressure differentials across the ends of the cuff create a "pistoning" effect in the cuff, which can shift the cuff up and down in the trachea, causing trauma to the patient, as well as irritation to the patient's trachea.

SUMMARY

This invention provides a tracheal tube having an improved cuff configuration which precludes movement of the cuff in the trachea during use and which, in turn, substantially prevents trauma and irritation to the patient.

Generally speaking, this invention provides a tracheal tube which includes an elongated tube for extending into the trachea of a patient to deliver air into the lungs of the patient. A flexible cuff is fixed to and surrounds the tube adjacent a posterior end of the tube and has anterior and posterior ends sealed to the tube to form a continuous hollow interior between the ends of the cuff for receiving a supply of field. Means are provided for filling the hollow interior of the cuff with fluid to inflate the cuff outwardly to seal the cuff against the patient's trachea. The cuff has an inflated configuration defining a bulbed anterior portion for sealing to the trachea. The bulbed portion is continuous with and in fluid communication which extends distally away from the bulbed anterior portion. The length of the cuff between the posterior and anterior ends thereof is substantially greater than the extent of the cuff occupied by the bulbed anterior portion. The bulbed portion in an unconfined inflated state of the cuff has a diameter substantially greater than that of the portion of the cuff posteriorly of the bulbed portion.

The improved cuff configuration also allows the cuff, in its collapsed state, to hold closely to the walls of the tracheal tube. This assures good visibility to the posterior end of the tracheal tube during the insertion process.

These and other aspects of the invention will be more fully understood by referring to the following detailed description and the accompanying drawings.

DRAWINGS

FIG. 2 is an enlarged fragmentary, cross-sectional elevation view showing the portion of the tracheal tube device within the circle 2 of FIG. 1; and FIG. 3 is an enlarged fragmentary, cross-sectional elevation view showing the portion of the inflated cuff within the circle 3 of FIG. 1.

DETAILED DESCRIPTION

Figure 1:
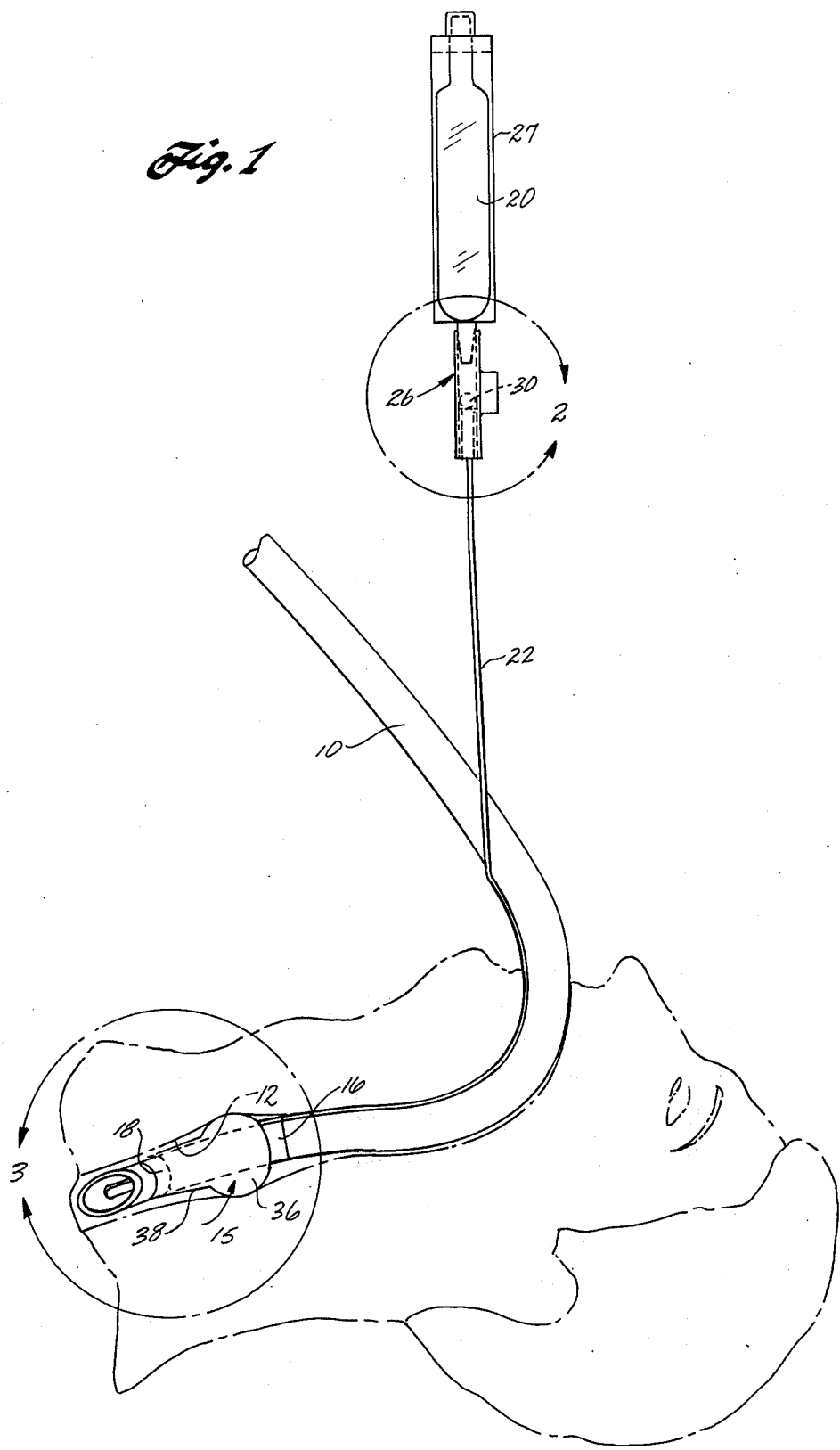
FIG. 1 is a fragmentary, semi-schematic, cross-sectional elevation view showing a tracheal tube device according to this invention inserted into the trachea of a patient and in which the cuff of the tube is shown in its inflated configuration.

Referring to FIG. 1, a tracheal tube 10 of well known curved configuration is sized and shaped to fit into the trachea 12 of a patient 14. A flexible, liquid-fillable cuff 15 surrounds the exterior of the tube. The drawings illustrate a hydraulic cuff, but the invention is equally applicable to pneumatic cuff tracheal tubes. The cuff 15 is sealed to the posterior region of the tube 10 which, during use of the tube, is fitted into the patient's trachea. The cuff 15 has anterior and posterior ends 16 and 18, respectively, which are sealed to the exterior of the tracheal tube. The ends of the cuff preferably are bonded to the tube by solvent evaporation techniques.

The cuff has a hollow interior, which is continuous from one end to the other of the cuff, for receiving liquid for inflating the cuff outwardly away from the tube and against the patient's trachea. The cuff is inflated by a source of liquid, preferably a saline solution, contained in a collapsible reservoir 20 or other similar device for holding a sufficient volume of liquid to inflate the cuff. An elongated filling lumen 22 transmits liquid from the reservoir 20 to the hollow interior of the cuff 15.

The preferred means for filling the cuff 15 is understood best by referring to FIG. 2. The collapsible liquid-filled reservoir 20 is shaped as a syringe and includes an elongated filler tube 24 extending from the base of the reservoir 20 into one end of a valve 26 for controlling the flow of liquid from the reservoir to the interior of the cuff. The collapsible reservoir 20 is held in a plastic outer container 27 to prevent external pressure from being inadvertently applied to the outside of the reservoir 20.

The valve 26 includes a flexible molded plastic valve housing 28 having an internal valve seat 29 and a ball valve 30 movable in interior passage 32 toward and away from the valve seat 29. One end of the filler lumen 22 is fitted into the end of the valve housing 28 opposite the end which receives the reservoir filler tube 24. The opposite end of the lumen 22 is sealed through the anterior end 16 of the cuff 15 (as shown best in FIG. 3) so the lumen opens into the interior of the cuff. The valve housing includes a flexible tab 34 projecting laterally outwardly from about mid-point of the housing adjacent the ball valve 30.

When using the tracheal 10, the physician initially places the posterior portion of the tube into the patient's trachea with the cuff 15 being in its collapsed state. The cuff 15 is then filled with liquid 35 (see FIG. 3) from the reservoir 20 by holding the reservoir above the cuff and then squeezing the valve 26 by applying finger pressure to the outside of the valve housing 28 adjacent the tab 34 to squeeze the ball valve 30 away from the valve seat 29. This allows water from the reservoir 20 to trickle from the reservoir through the filling lumen 22 and into the cuff to inflate the cuff against the patient's trachea.

FIGS. 1 and 3 show the inflated configuration of the cuff 15, which is the subject of this invention. The cuff has a bulbed anterior portion 36, and an elongated, narrowed posterior portion 38 extending distally away from the bulb. The bulbed anterior portion 36 is generally spherical-shaped; and the narrowed posterior portion 38 is generally conical-shaped and tapers narrower distally away from the bulb. The posterior portion 38 of the inflated cuff tapers down to the same dimension as the outside diameter of the tube 10 at the distal end of the cuff. Only the bulbed portion of the cuff seals against the walls of the patient's trachea.

As to the preferred dimensions of the inflated cuff 15, the minimum diameter of the tapered narrowed posterior portion 38 (dimension B in FIG. 3) is about 1¼ times the outside diameter of the tube 10 (dimension A in FIG. 3). The maximum diameter of the narrowed posterior portion 38, at the point of abrupt enlargement into the bulb (dimension C in FIG. 3), is about 1½ times the outside diameter of the tube. The bulbed portion 36 is shaped generally spherically and has a maximum diameter (dimension D in FIG. 3) of about 2½ times the outside diameter of the tube. The length of the cuff (dimension E in FIG. 3) varies from about 3 to 4 times the outside diameter of the tube.

The dimensions of the inflated cuff vary in size depending upon the patient the tube is used with. Typically, the outside diameter of the tracheal tube varies between about 3/10 to ½ inch. The minimum diameter of the tapered narrowed posterior portion 38 varies between about ⅜ to 6/10 inch, and the maximum diameter of the narrowed portion varies between about ½ to 7/10 inch. The maximum diameter of the bulb is about 1½ to 2 times the maximum diameter of the narrowed portion 38, and varies between about 8/10 to 1 2/10 inches.

In the preferred method of making the cuff, a mandrel is shaped in the inflated configuration of the cuff. The mandrel is heated and then dipped into a bath of liquid polyvinyl chloride, or any other suitable plastic or synthetic rubber material which is of thin, pliable sheet form. A suitable release agent, such as non-toxic silicone-based release material, may be used on the mandrel prior to dipping it in the bath of polyvinvyl chloride. After the coated mandrel is removed from the bath, the plastic coating is cured with heat, and the cured plastic membrane is stripped from the mandrel when cool. The ends of the cuff are then bonded to the exterior of the tracheal tube by appropriate techniques.

The novel configuration of the inflated cuff 15 precludes movement of the cuff in the patient—s trachea during use. In prior art cuffs which are of substantially uniform diameter from end-to-end, a substantial effective area of the cuff is sealed against the trachea when the cuff is inflated. This area is sensitive to the pressure differentials across the cuff which are produced in the trachea during the inspiration and expiration phases of the patient's respiration cycle. These pressure differentials across the ends of a conventional cuff can create a pistoning effect in the cuff which tends to shift the cuff up and down in the trachea, thereby causing trauma to the patient. In the cuff of this invention, only a relatively small effective area, namely, the maximum diameter of the bulbed portion 36, seals against the patient's trachea. This configuration of the cuff allows a redistribution of the filling fluid in the interior of the cuff due to the pressure differential acting on the bulb during the inhalation and exhalation cycles. As a result, the cuff is more likely to stay in exactly the location where it is first placed by the physician, and not to slide back and forth in the trachea. This, in turn, reduces the trauma and irritation to the patient.

As a further advantage, the cuff of this invention, in its collapsed state, holds closely to the walls of the tracheal tube. The flaccid, collapsed bulbed portion of the cuff is able to be folded back on itself permitting the entire cuff to hold closely to the exterior of the tube. This assures good visibility to the posterior end of the tube when the physician inserts the tube into the patient's trachea.

What is claimed is:

1. A tracheal tube in combination comprising an elongated tube for extending into the trachea of a patient to deliver air into the lungs of the patient; a flexible cuff fixed to and surrounding the tube adjacent a posterior end of the tube and having anterior and posterior ends sealed to the tube to form a continuous hollow interior between the ends of the cuff for receiving a supply of fluid; and means for filling the hollow interior of the cuff with fluid to inflate the cuff outwardly to seal the cuff against the patient's trachea, the cuff having an inflated configuration defining a bulbed anterior portion for sealing to the trachea and being continuous with and in fluid communication with a narrowed posterior portion extending distally away from the bulbed anterior portion, the length of the cuff between the posterior and anterior ends thereof being substantially greater than the extent of the cuff length occupied by the bulbed anterior portion of the cuff, the bulbed portion having in an unconfined inflated state of the cuff a diameter substantially greater than that of the portion of the cuff posteriorally of the bulbed portion.

2. The tracheal tube according to claim 1 in which the bulbed anterior portion of the cuff is generally spherical in shape.

3. The tracheal tube according to claim 2 in which the diameter of the bulb is about 1½ to 2 times the maximum diameter of the narrowed posterior portion of the cuff.

4. The tracheal tube according to claim 3 in which the maximum diameter of the narrowed posterior portion of the cuff is about 1½ times the outside diameter of the tube.

5. The tracheal tube according to claim 4 in which the length of the cuff is about 3 to 4 times the outside diameter of the tube.

6. The tracheal tube according to claim 1 in which the cuff is shaped so the maximum cross-sectional dimension of the narrowed posterior portion abruptly expands outwardly into the bulbed exterior configuration of the anterior portion.

7. The tracheal tube according to claim 6 in which the narrowed posterior portion tapers narrower distally away from the bulbed anterior portion.

8. The tracheal tube according to claim 6 in which the diameter of the bulb is about 1½ to 2 times the maximum diameter of the narrowed posterior portion of the cuff.

9. The tracheal tube according to claim 6 in which the length of the bulb is about half the length of the narrowed posterior portion.

10. The tracheal tube according to claim 6 in which the maximum diameter of the narrowed portion, at the point of enlargement into the bulb, is about 1½ times the outside diameter of the tube, and the diameter of the bulb is about 2½ times the outside diameter of the tube.

11. The tracheal tube according to claim 1 in which the means for filling the cuff comprises a reservoir for holding a supply of liquid, and an elongated filling lumen extending from the reservoir into the bulbed anterior portion of the cuff.

12. The tracheal tube according to claim 11 including a flexible valve housing between the reservoir and the lumen, a ball valve in the interior of the valve housing and movable from a valve seat in the housing in response to exterior pressure applied to the housing to allow liquid to flow through the lumen into the cuff.

13. In a hydraulic cuff tracheal device having an elongated tube for extending into the trachea of a patient to deliver air to the lungs of the patient, and an elongate flexible cuff fixed to and surrounding the exterior of the tube adjacent a posterior end of the tube and sealed to the tube to form a hollow interior for receiving a supply of liquid to inflate the cuff outwardly to seal it against the trachea, an improved cuff configuration in which the cuff, in its inflated condition, is shaped to form a bulbed anterior portion for sealing against the patient's trachea, the anterior portion being continuous with and in fluid communication with a narrowed posterior portion extending distally away from the bulbed portion, the length of the cuff along the tube between the opposite ends thereof being substantialy greater than the extent of the cuff length occupied by the bulbed anterior portion of the cuff, the bulbed portion having in an unconfined inflated state of the cuff a diameter substantially greater than that of the portion of the cuff posteriorly of the bulbed portion.

14. The improvement according to claim 13 in which the bulbed anterior portion of the cuff is generally spherical in shape.

15. The improvement according to claim 13 in which the cuff is shaped so that the maximum cross-sectional dimension of the narrowed posterior portion of the cuff abruptly expands to form the bulbed portion of the cuff.

16. The improvement according to claim 15 in which the narrowed posterior portion tapes narrower away from the bulb.

17. The improvement according to claim 16 in which the maximum diameter of the bulb is about 1½ to 2 times the maximum diameter of the narrowed posterior portion of the cuff.

18. The improvement according to claim 17 in which the length of the bulb is about half the length of the narrowed posterior portion of the cuff.

19. The improvement according to claim 16 in which the maximum diameter of the narrowed portion, at the point of enlargement into the bulb, is about 1½ times the outside diameter of the tube, and the diameter of the bulb is about 2½ times the outside diameter of the tube.

20. The improvement according to claim 16 in which the length of the inflatable cuff is about 3 to 4 times the outside diameter of the tube.

* * * * *

UNITED STATES PATENT AND TRADEMARK OFFICE
Certficate

Patent No. 4,022,217                                   Patented May 10, 1977

Donald R. Rowean

Application having been made by Donald R. Rowean, the inventor named in the patent above identified, and Dupaco Incorporated, San Marces, California, a corp. of California, the assignee, for the issuance of a certificate under the provisions of Title 35, Section 256, of the United States Code, adding the name of Richard R. Jackson as a joint inventor, and a showing and proof of facts satisfying the requirements of the said section having been submitted, it is this 26th day of August 1980, certified that the name of the said Richard R. Jackson is hereby added to the said patent as a joint inventor with the said Donald R. Rowean.

FRED W. SHERLING,
*Associate Solicitor.*